US00PP10733P

United States Patent [19]

Nowlin

[11] Patent Number: Plant 10,733

[45] Date of Patent: Dec. 22, 1998

[54] *RHAPHIOLEPIS INDICA* PLANT NAMED 'CREEKLIN''

[75] Inventor: Jeff Nowlin, Conroe, Tex.

[73] Assignee: Turkey Creek Farms, Inc., Humble, Tex.

[21] Appl. No.: 876,302

[22] Filed: Jun. 16, 1997

[51] Int. Cl.[6] ..... A01H 5/00

[52] U.S. Cl. ..... Plt./67.5

[58] Field of Search ..... Plt./67.5

[56] References Cited

U.S. PATENT DOCUMENTS

P.P. 1,138 10/1952 Marken et al. ..... Plt./67.5
P.P. 5,215 4/1984 Usrey ..... Plt./67.5
P.P. 8,635 3/1994 Barr ..... Plt./67.5

*Primary Examiner*—Howard J. Locker
*Assistant Examiner*—Kent L. Bell
*Attorney, Agent, or Firm*—C. A. Whealy

[57] ABSTRACT

A distinctive cultivar of Hawthorne, *Rhaphiolepis indica*, plant named 'Creeklin'', characterized by its erect, dense, mounded and uniform plant habit; fine plant texture which allows for ease of shearing; small, oblong, mostly flat leaves with an acute apex are initially coppery and mature to a shiny dark green color; dark reddish brown young stem color; and numerous light pink flowers. The combination of light pink flowers with dark brownish red stems, coppery new growth and shiny dark green mature foliage provides the new Hawthorne a striking and unique appearance.

3 Drawing Sheets

The present invention relates to a new and distinctive cdultivar of Hawthorne plant, botanically known as *Rhaphiolepis indica*, and hereinafter referred to by the cultivar name 'Creeklin''. It is proposed that the cultivar 'Creeklin'' will be marketed under the trade name CandleLight.

The new cultivar was discovered by the inventor in Humble, Tex., as a naturally-occurring mutation of the nonpatented *Rhaphiolepis indica* cultivar 'Harbinger of Spring', and was observed in a group of plants of the parent cultivar in March, 1992.

Asexual reproduction of the new cultivar by cuttings in Humble, Tex., has shown that the unique features of this new Hawthorne are stable and are reproduced true to type in successive propagations.

The new cultivar has not been observed under all possible environmental conditions. The phenotype may vary significantly with variations in environment such as temperature and light and fertility levels, without, however, any variance in genotype.

The following traits have been repeatedly observed and are determined to be the unique characteristics of 'Creeklin'':

1. Erect, dense, mounded and uniform plant habit.
2. Fine plant texture which allows for ease of shearing.
3. Desirable plant height which can be maintained at 90 to 120 cm with shearing; unsheared plants will grow to 180 to 240 cm.
4. Small, oblong, flat leaves with an acute apex that are initially coppery and mature to a shiny dark green color.
5. Dark reddish brown young stem color.
6. Numerous light pink flowers.
7. Combination of light pink flowers with dark brownish red stems, coppery new growth and shiny dark green mature foliage provides the new Hawthorne a striking and unique appearance.

The following characteristics differentiate the new Hawthorne from the parent cultivar 'Harbinger of Spring' and other Hawthornes commercially known and used in the nursery industry:

1. Plants of the new Hawthorne are denser and more mounding than plants of the cultivar 'Harbinger of Spring'. Plants of the cultivar 'Harbinger of Spring' have an open plant habit.

2. Plants of the new Hawthorne have a more uniform plant shape than plants of the cultivar 'Harbinger of Spring'.
3. Plants of the new Hawthorne are easier to shear and shape than plants of the cultivar 'Harbinger of Spring' as plants of the new Hawthorne have a smaller and finer leaf texture than plants of the cultivar 'Harbinger of Spring' which have a coarser texture.
4. Plants of the new Hawthorne have leaves that are shorter, narrower and flatter than leaves of plants of the cultivar 'Harbinger of Spring'. Additionally, plants of the new Hawthorne have oblong-shaped leaves whereas plants of the cultivar 'Harbinger of Spring' have oblanceolate-shaped leaves.
5. Young leaves of the new Hawthorne are coppery and mature to a shiny dark green color, whereas leaves of the cultivar 'Harbinger of Spring' have tan-colored young leaves that are dull and paler green at maturity.
6. Young stems of plants of the new Hawthorne are shiny brownish red whereas young stems of plants of the cultivar 'Harbinger of Spring' are dull greenish brown in color.
7. Flowers of plants of the new Hawthorne have five petals whereas flowers of plants of the cultivar 'Harbinger of Spring' have five to seven petals.

The accompanying colored photographs illustrate the overall appearance and flower color of the new Hawthorne, showing the colors as true as it is reasonably possible to obtain in colored reproductions of this type.

The photograph at the top of the first sheet of photographs comprises a top perspective view of a typical containerized plant of 'Creeklin''.

The photograph at the bottom of the first sheet of photographs comprises a side perspective view of typical flowering containers of the cultivars 'Creeklin'' (left) and 'Harbinger of Spring' (right) showing the differences in plant habit and shape.

The photograph at the top of the second sheet is a close-up view of typical leaves of the cultivars 'Creeklin'' (left) and 'Harbinger of Spring' (right) showing the differences in leaf shape, size and serration.

The photograph at the bottom of the second sheet is a close-up view of typical stems of the cultivars 'Creeklin'' (left) and 'Harbinger of Spring' (right) showing the differences in stem color.

The photographs on the third sheet are close-up views of typical plants of the cultivars 'Creeklin'' (top) and 'Harbinger of Spring' (bottom) showing the differences in flower petalage and foliage color. Actual flower and foliage colors may differ from flower and foliage colors in the photographs due to light reflectance.

The following observations, measurements, values, and comparisons describe plants grown in Humble, Tex., under commercial practice. The plants were initially grown in a polyethylene-covered greenhouse and then moved to a field situation. In the greenhouse, day and night temperatures ranged from 18 to 21° C. and 14 to 17° C., respectively, and light levels were maintained at 3,500 4,000 footcandles. In the following description, color references are made to The Royal Horticultural Society Colour Chart except where general terms of ordinary dictionary significance are used.

Botanical classification: *Rhaphiolepis indica* cultivar 'Creeklin''.

Parentage: Naturally-occurring mutation of nonpatented *Rhaphiolepis indica* cultivar 'Harbinger of Spring'.

Propagation:

*Type.*—By cuttings.

*Time to initiate roots.*—21 and 42 days at temperatures of 27 and 10°C., respectively.

*Time to develop roots.*—42 and 82 days at temperatures of 27 and 10°C., respectively.

*Rooting habit.*—Root system is coarse and moderately fibrous.

Plant description:

*Plant form.*—Upright and mounded shrub. Freely branching, plants are dense and not open. Usually at least three lateral shoots are formed when the terminal apex is removed. Plants uniform is shape. Flowers abundant.

*Growth habit.*—Lateral shoots upright, the more outward forming rounded shape. Moderate to vigorous.

*Plant height.*—Shearing can maintain plants at 90 to 120 cm, without shearing, plants grow to 180 to 240 cm.

*Stem description.*—Lateral branch diameter: About 4 mm. Internode length: About 1.6 cm. Stem color: Dark brownish red, 183A. Stem texture: Shiny, slightly pubescent.

*Foliage description.*—Leaf arrangement: Simple, alternate. Leaf length: About 5 cm. Leaf width: About 2.5 cm. Leaf shape: Symmetrical, oblong. Leaf apex: Acute. Leaf base: Cuneate. Leaf margin: Crenate/serrate. Leaf aspect: Mostly flat. Leaf texture: Young foliage: Fine, brownish pubescence give new growth a coppery appearance. Mature foliage: Shiny, leathery, smooth, durable. Leaf color: Young foliage, adaxial surface: Shiny and red, 180A to 152A with reddish tones. Young foliage, abaxial surface: Red, 180A to 146C with reddish tones. Mature foliage, adaxial surface: Shiny and darker than 147A. Mature foliage, abaxial surface: 147B. Venation, adaxial surface: 146A. Venation, abaxial surface: 147B. Petiole length: About 1 cm. Petiole diameter: About 2 mm. Petiole color: 146A.

Flower description:

*Flowering habit.*—Star-shaped flowers arranged in singly on panicles. Slight fragrance. Flowers held upright. Flowers persistent.

*Natural flowering season.*—Early spring.

*Quantity of flowers.*—Numerous, usually about 60 flowers per panicle. Number of panicles depends on plant size and number of lateral branches developed.

*Flowers.*—Diameter: About 2 cm. Height: About 1 cm.

*Peduncle.*—Peduncle angle: About 45°. Strength: Flexible, but hold flowers upright. Color: 146A.

*Flower bud.*—Shape: Oblong. Diameter: About 4 mm. Length: About 1.2 cm. Color: 65A.

*Petals.*—Arrangement: In a circle, not fused. Shape: Ovate. Quantity per flower: Five. Length: About 1 cm. Width: About 5 cm. Apex: Acute. Margin: Entire to finely serrate. Texture: Smooth, satiny, pubescent at basal margins. Color: When opening: Adaxial surface: 65A. Abaxial surfaces: 65B. Fully open: Adaxial surface: 65B to 155D. Abaxial surface: Very light pink to white.

*Sepals.*—Arrangement: Fused into a calyx, star-shaped. Shape: Lanceolate. Quantity per flower: Five. Calyx length: About 7 mm. Calyx diameter: About 4 mm. Apex: Acute. Margin: Pubescent/ciliate. Texture: Smooth, but pubescence at margins. Color: Adaxial surface: 146A, red, 59A, at margins with a red, 59A, ring where sepals are fused. Abaxial surface: 146B.

*Reproductive organs.*—Stamens: Quantity: About 10. Anther shape: Bilobate. Anther size: About 1 by 0.75 mm. Anther color: 8A. Pollen amount: Moderate. Pollen color: 12A. Pistils: Length: About 5 mm. Stigma shape: Round. Stigma color: Light green. Style color: Light green. Ovary color; Light green.

Disease resistance: Resistance to known pathogens of Hawthorne has not been observed.

Seed production: Seed production has not been observed.

I claim:

1. A new and distinct Hawthorne, *Rhaphiolepis indica* plant named 'Creeklin'', as illustrated and described.

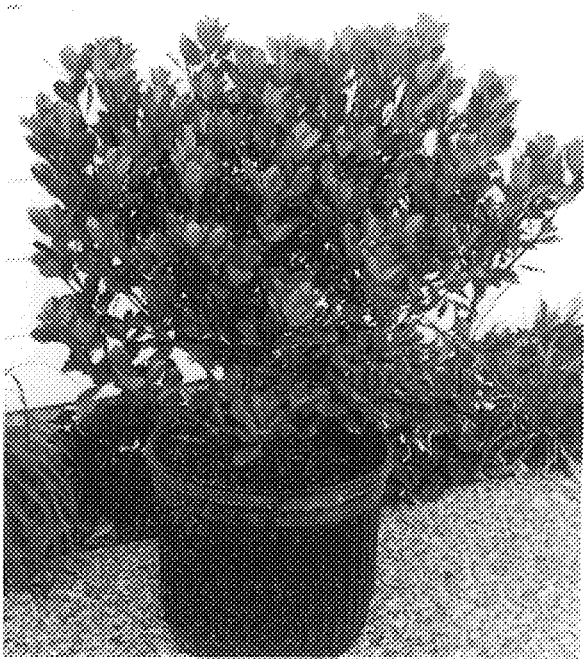
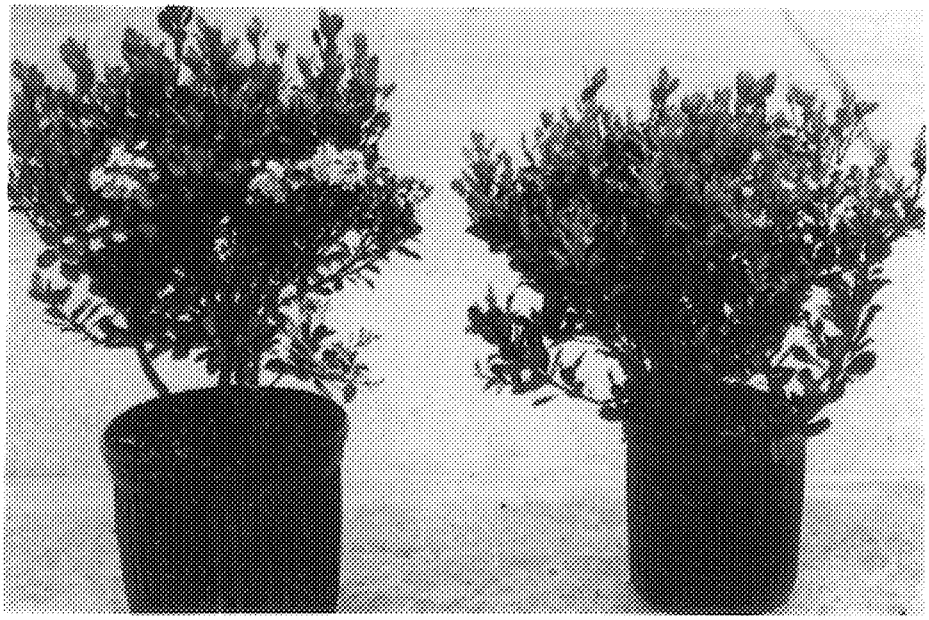

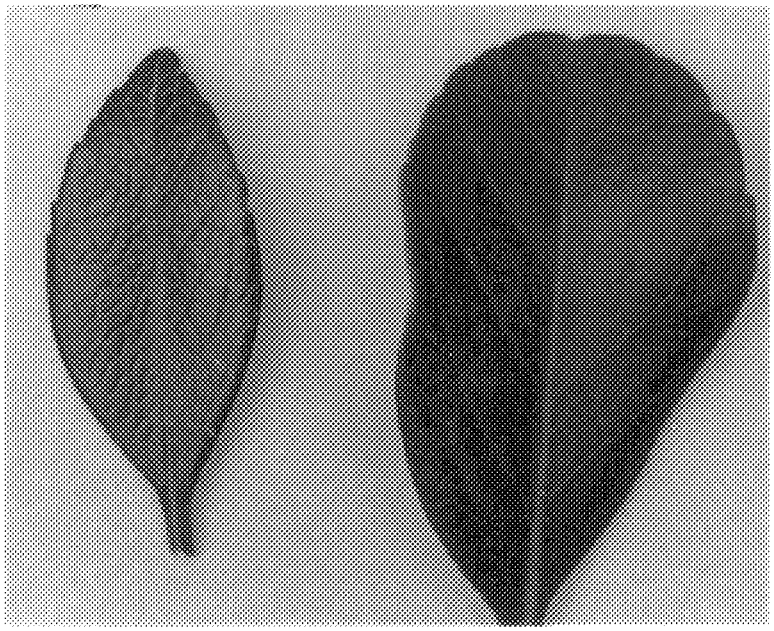
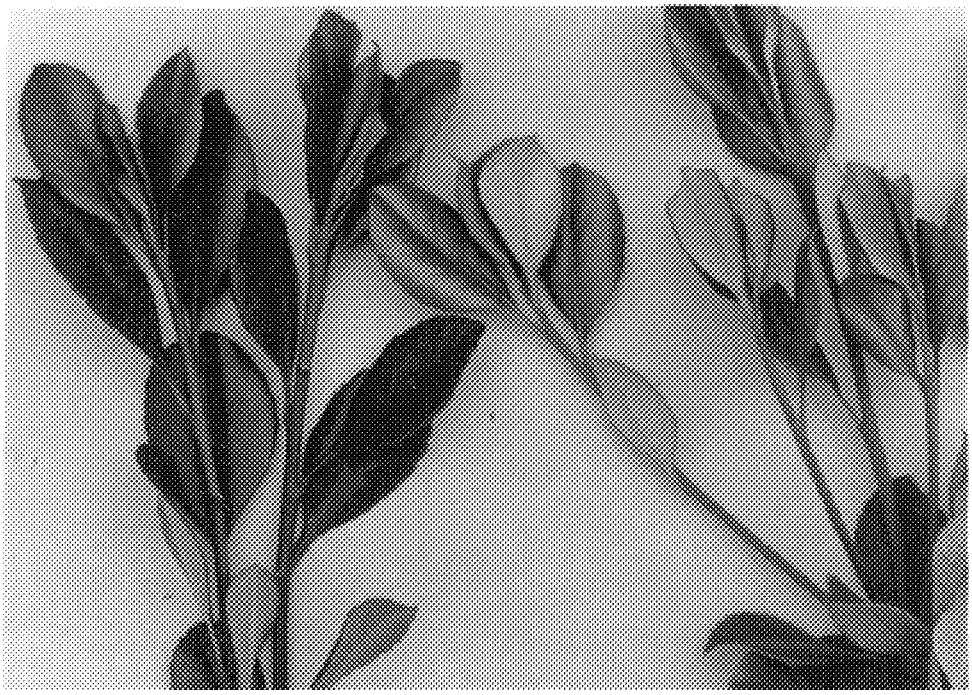

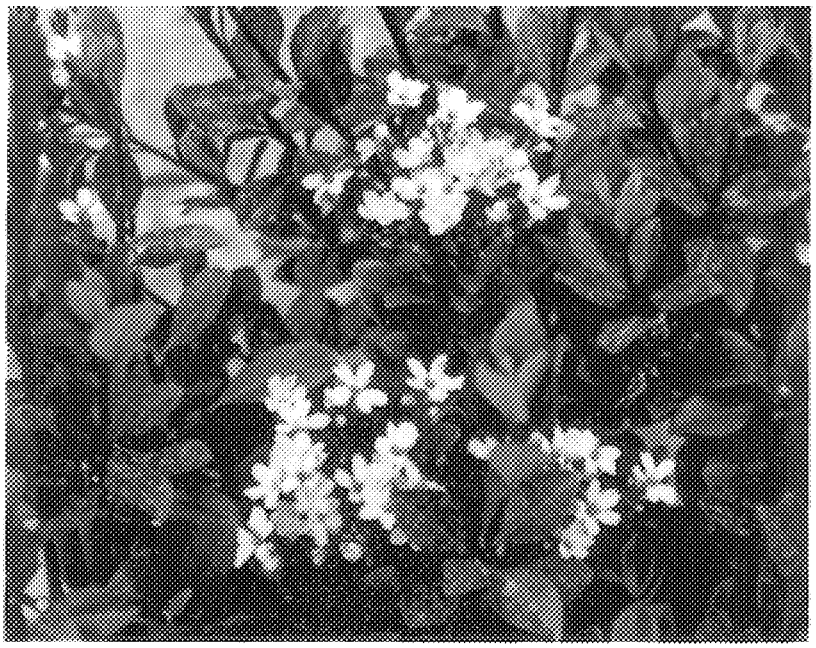
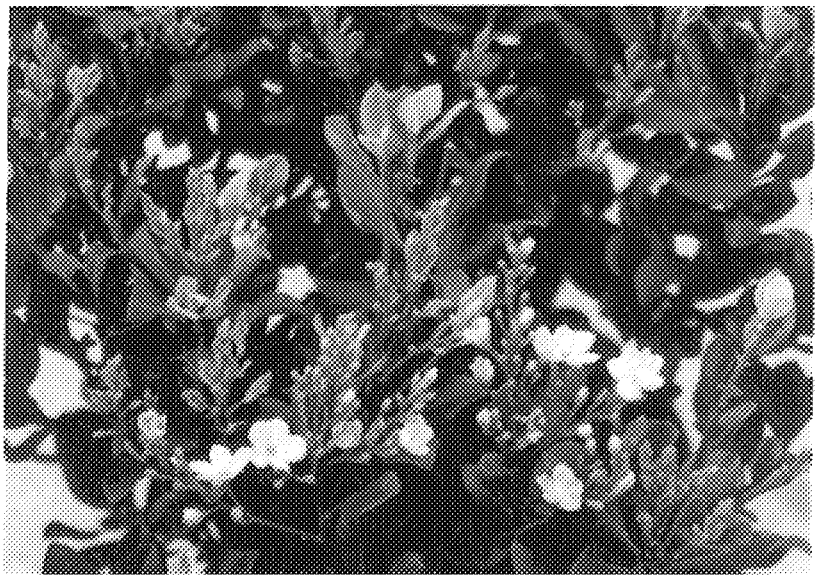

* * * * *